United States Patent [19]

Mount, II

[11] Patent Number: 4,973,960
[45] Date of Patent: Nov. 27, 1990

[54] DATA ENTRY METHOD AND APPARATUS

[75] Inventor: Houston B. Mount, II, Tulsa, Okla.

[73] Assignee: Amoco Corporation, Chicago, Ill.

[21] Appl. No.: 315,883

[22] Filed: Feb. 24, 1989

[51] Int. Cl.$^5$ .............................................. G06F 3/02
[52] U.S. Cl. ...................................... 341/23; 341/22; 340/711
[58] Field of Search ................... 341/22, 23, 5, 34, 26; 340/711, 712, 853, 860; 73/151; 367/33, 81

[56] References Cited

U.S. PATENT DOCUMENTS

| | | | |
|---|---|---|---|
| 3,560,964 | 2/1971 | Bedell et al. | 341/23 |
| 4,136,336 | 1/1979 | Abe et al. | 341/5 |
| 4,274,081 | 6/1981 | Nomura et al. | 341/22 |
| 4,310,839 | 1/1982 | Schwerdt | 341/22 |
| 4,621,178 | 11/1986 | Taguchi et al. | 341/34 |
| 4,725,817 | 2/1988 | Wihlborg | 341/34 |

FOREIGN PATENT DOCUMENTS

| | | | |
|---|---|---|---|
| 0056327 | 5/1979 | Japan | 341/23 |
| 0056228 | 4/1980 | Japan | 341/23 |
| 0067823 | 5/1980 | Japan | 341/26 |
| 0095635 | 6/1984 | Japan | 341/23 |
| 0105164 | 6/1984 | Japan | 341/23 |
| 2127598 | 4/1984 | United Kingdom | 341/34 |

Primary Examiner—Donald J. Yusko
Assistant Examiner—Yuk H. Lau

[57] ABSTRACT

A housing includes a liquid crystal display, a keypad and a three ring notebook a plurality of pages therein. Each page includes a plurality of descriptors. A touch sensitive linear potentiometer is affixed to the housing adjacent a page bay into which the book pages can be received one at a time. Data concerning an observed characteristic of a geological core sample is entered into a computer memory by selecting a page and thereafter depressing the strip adjacent the descriptor of interest.

8 Claims, 5 Drawing Sheets

```
550:WACKEST:::::GRY:DARK:ARGIL:PARA BED::BIOTUR:::::OTHER:::::
551:WACKEST:::::GRY:MEDIUM:ARGIL:PARA BED::BIOTUR:::::MARINE:::::
552:WACKEST:::::GRY:MEDIUM:ARGIL:PARA BED:::::MARINE:::::
553:WACKEST:::::GRY:MEDIUM:ARGIL:PARA BED::BIOTUR:::::MARINE:::::
554:WACKEST:::::GRY:MEDIUM:ARGIL:::BIOTUR:::::MARINE:::::
555:WACKEST:::::GRY:MEDIUM:ARGIL:PARA BED:::::MARINE:::::
556:WACKEST:::::GRY:MEDIUM:ARGIL:PARA BED:::::MARINE:::::
557:WACKEST:::::GRY:MEDIUM:ARGIL:PARA BED:::::MARINE:::::
558:WACKEST:::::GRY:MEDIUM:ARGIL:PARA BED:::::MARINE:::::
559:WACKEST:::::GRY:MEDIUM:ARGIL:PARA BED:::::MARINE:::::
560:WACKEST:::::GRY:MEDIUM:ARGIL:PARA BED:::::MARINE:::::
561:WACKEST:::::GRY:MEDIUM:ARGIL:PARA BED:MOLLUSKS:::PYR::MARINE:::::
562:WACKEST:::::GRY:MEDIUM:ARGIL:PARA BED::MARINE:::::
563:WACKEST:::::GRY:MEDIUM:ARGIL:PARA BED::BIOTUR:::::MARINE:::::
564:WACKEST:::::GRY:MEDIUM:ARGIL:PARA BED:MOLLUSKS:::::MARINE:::::
565:WACKEST:::::GRY:MEDIUM:ARGIL:PARA BED:::::MARINE:::::
566:WACKEST:::::GRY:MEDIUM:ARGIL:PARA BED::::PYR NOD:PYR::MARINE:::::
567:WACKEST:::::GRY:MEDIUM:ARGIL:PARA BED::::PYR NOD::MARINE:::::
568:WACKEST:::::GRY:MEDIUM:ARGIL:PARA BED:::::MARINE:::::
569:WACKEST:::::GRY:MEDIUM:ARGIL:PARA BED:MOLLUSKS:::::MARINE:::::
570:WACKEST:::::GRY:DARK:ARGIL:PARA BED::::CALC::MARINE:::::
571:WACKEST:::::GRY:DARK:ARGIL:PARA BED::::CALC::MARINE:::::
572:WACKEST:::::GRY:DARK:ARGIL:PARA BED::::CALC::MARINE:::::
573:WACKEST:::::GRY:DARK:ARGIL:PARA BED::::CALC::MARINE:::::
574:WACKEST:::::GRY:DARK:ARGIL:PARA BED::::CALC::MARINE:::::
575:WACKEST:::::GRY:MEDIUM:ARGIL:OTHER::BIOTUR:BURROWS, HORZ:::CALC::MARINE:::::
576:WACKEST:::::GRY:MEDIUM:ARGIL:WAVY BED::BIOTUR:::CALC::MARINE:::::
577:WACKEST:::::GRY:DARK:ARGIL:PARA BED::::CALC::MARINE:::::
```

FIG. 4

DATA ENTRY METHOD AND APPARATUS

BACKGROUND OF THE INVENTION

1. Field of the Invention

The instant invention pertains to data entry methods and apparatus and more particularly to such methods and apparatus which facilitate entry of data into a memory means by a human operator.

2. Description of Related Art

Computers, of both the dedicated or embedded variety as well as programmable computers, are used in a broad range of contexts. In connection with such uses, human operators are often required to enter data into a computer memory. For example, so-called "fast food" retailers, i.e., sellers of food for consumption on or off the premises, sometimes utilize a cash register having an array of buttons, each of which represents a menu item. As an order is placed, the operator punches the button, thereby storing into the computer memory the food item as well as a preselected price associated with the item. When the order is complete, a button is pressed which generates a printout specifying the food ordered, the cost of each item, and the total cost.

Such a system is adequate for handling a relatively small number of preselected data inputs, i.e., the various food items, because each item can be represented by a separate button on the machine. However, use of such a system would not be feasible if the preselected data inputs from which an operator was required to choose and enter into a computer memory numbered in the hundreds or thousands.

Some computer systems enable a user to call up different screens and thereafter touch points on the screen to effect different computer operations. Such a system could be adapted to enter preselected data inputs displayed on the screen; however, such a system is not hand-holdable and is limited in the type and quality of information which can be displayed when compared to the broad range of information printable on or fixable to a tangible medium such as paper, e.g., varying shades of colors, textures, etc.

In connection with entry of data into a computer by an operator, it is typically necessary for the operator to collect information about an object or event and thereafter enter data relating to the collected information. In the fast food cash register example described above, the operator must hear or observe the customer place an order and thereafter make the appropriate entry.

Another situation in which information is collected and thereafter entered into a computer relates to geological characteristics observed in connection with core removed from a borehole in an earth formation. Some coring methods are capable of generating thousands of feet of core over a few weeks time on a given well. It is not practical to transport and store this much core nor is it desirable to handle it any more than necessary. Thus, it is desirable to evaluate the core at the well site as the core is recovered. Part of this evaluation includes a detailed description of the appearance of the core. This is typically done by a geologist who, in the past, dictated the description into a tape recorder or wrote the same onto a clipboard check sheet. The data is thereafter transcribed by a computer operator to enter it in a computer memory. This typically occurs in an office rather than at the well site.

There exist some prior art voice recognition systems which can be used to input data derived from the voice of a geologist directly into a computer and thereby avoid the transcription process. However, voice actuated systems require considerable training to operate and hours of collecting voice patterns from each person who may use them.

There exists a need for a data entry method and apparatus which would overcome the above enumerated problems inherent in such prior art methods and apparatus.

There exists a need for such a method and apparatus which would permit an operator to make data entries into a memory means with relatively little training.

There exists a need for such a method and apparatus which may be hand-held or placed on an operator's lap to facilitate field use of the same.

SUMMARY OF THE INVENTION

The method of the invention comprises providing a book having a plurality of pages each of which includes at least one descriptor. Information about an object or event is collected and thereafter one of the pages is selected. The page is moved into a page bay, and information identifying the selected page is provided to a memory means. Descriptor selection means is provided adjacent the page bay and is actuable to identify a selected one of the descriptors on such a page when the same is received in said page bay. A descriptor is selected from the page which relates to such collected information and the selection means is actuated to identify the selected descriptor. Thereafter, information identifying the selected descriptor is provided to the memory means.

Apparatus is provided for performing the method of the invention.

The foregoing and other features and advantages of the invention will become more readily apparent from the following detailed description of a preferred embodiment which proceeds with reference to the drawings.

BRIEF DESCRIPTION OF THE DRAWING

FIG. 4 is a copy of a print-out of data entered into the memory of the schematically-illustrated computer in FIG. 2 by the device of FIG. 1.

DESCRIPTION OF THE PREFERRED EMBODIMENT

Figure 1:
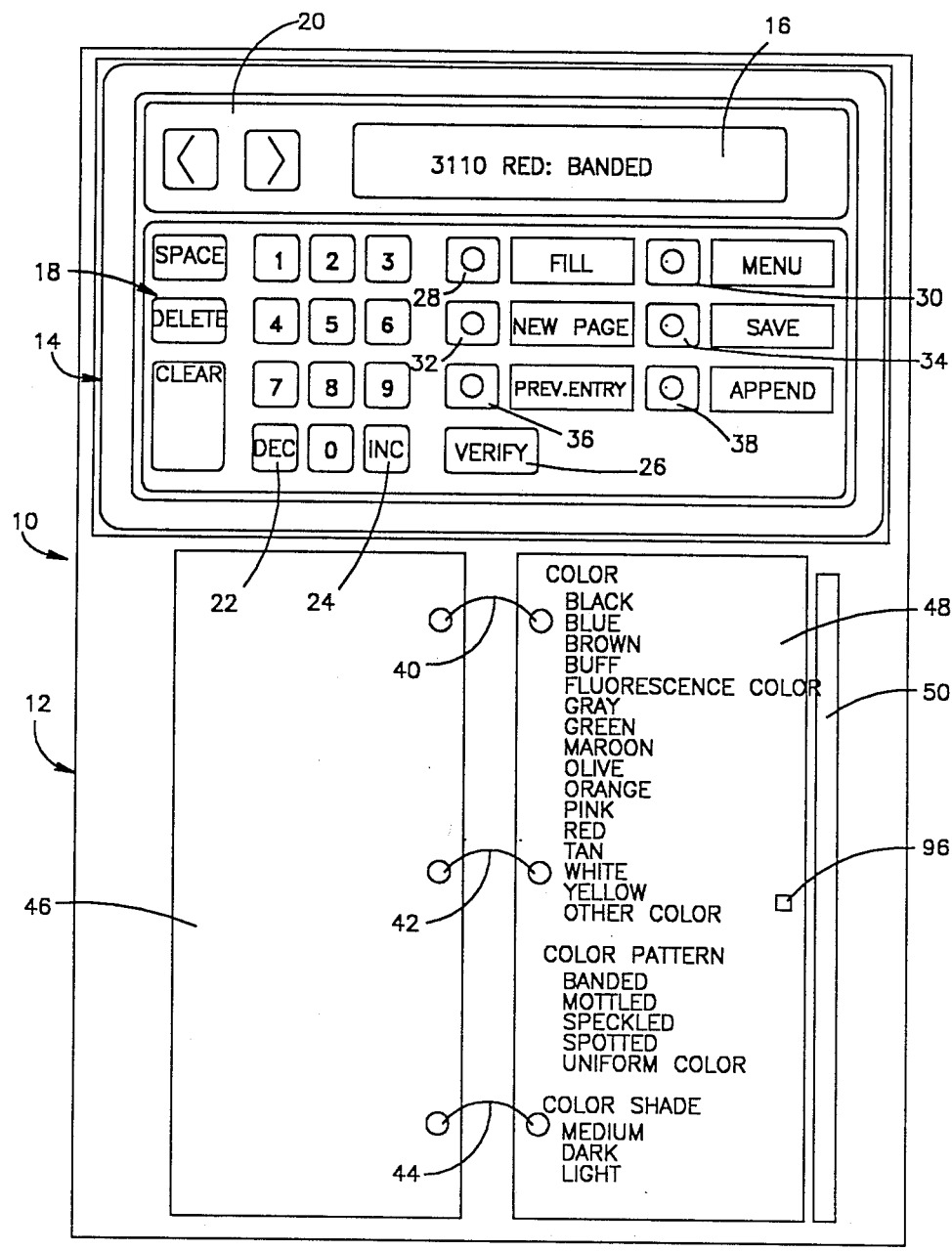
FIG. 1 is a top plan view of a portion of a device constructed in accordance with the apparatus of the instant invention.

Turning now to FIG. 1, indicated generally at 10, is a data entry device or clipboard constructed in accordance with the instant invention. Included in device 10 is a housing 12 having a commercially available keyboard/display 14 mounted thereon. Keyboard/display 14 includes thereon a liquid crystal display 16 and a keyboard, such being generally indicated at 18. Display 16 can display 16 alpha-numeric characters at a time. Keyboard/display 14 includes a buffer (not shown)

which can store up to 80 alpha-numeric characters that can be scrolled onto the display using scroll keys 20.

Keyboard 18 includes keys for numerals 0 through 9 as shown. Command keys on keyboard 18 include a depth decrement (DEC) key 22; a depth increment (inc) key 24; a VERIFY key 26, such being also referred to herein as a verifier; a FILL key 28; a MENU key 30; a NEW PAGE key 32; a save key 34; a PREVIOUS ENTRY key 36 and an APPEND key 38, such also referred to herein as appender means. Information concerning the function of each of the foregoing keys will be provided hereinafter in connection with the description of the operation of device 10.

Mounted on the upper side of housing 12 are three rings 40, 42, and 44 of the type which may be opened, to receive three-punched sheets, and thereafter closed to permit turning of the sheets from page to page as in a book. A plurality of such sheets or pages, two of which are pages 46, the back of which is visible, and page 48, the front of which is visible, are received on rings 40, 42, and 44. It is to be appreciated that additional sheets are received under sheet 48 as well as under sheet 46 with each such sheet having information printed on the front thereof, like sheet 48. That portion of the clipboard over which sheet 48 is received is referred to herein as a page bay. When it is desired to reference information on the front of a particular page, the pages are turned until the page of interest is received, with its front visible, over the page bay. All of the pages contained on rings 40, 42, and 44 are referred to herein as a book.

Figure 2:
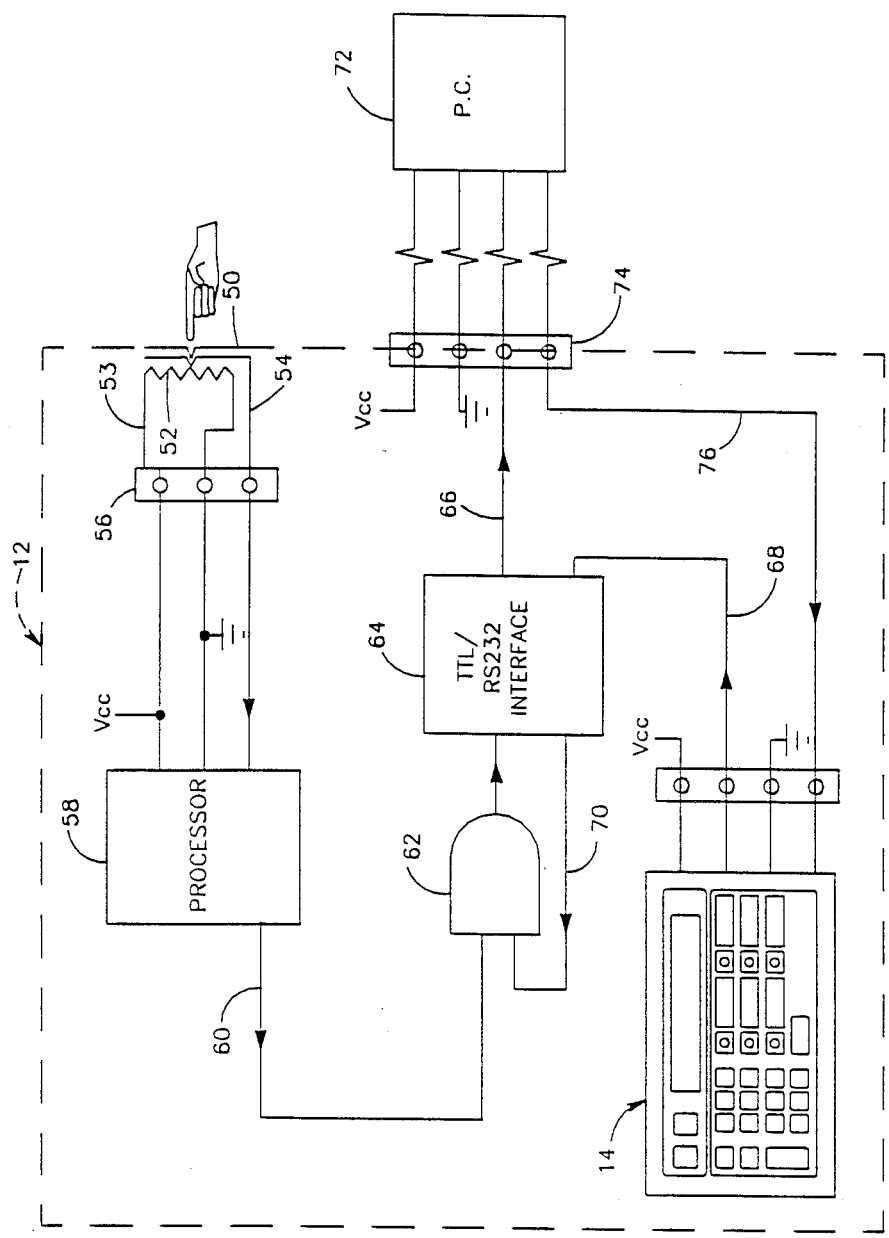
FIG. 2 is a schematic diagram of the device illustrated in FIG. 1 and further schematically illustrates its connection to a computer.

A commercially available linear potentiometer or selection strip 50 is mounted on housing 12. Strip 50 is referred to herein as data input selecting means and descriptor selection means. Strip 50 is schematically illustrated in FIG. 2 and includes therein a lower resistive element 52 mounted on housing 12 along the length of strip 50. An upper conductive element, the upper surface of which is visible in FIG. 1, is schematically illustrated by wiper arm connected to conductor 54 in FIG. 2. Strip 50 includes three conductive leads which are connected as shown in FIG. 2, one lead being attached to one end of resistive element 52 (and being grounded), one lead being attached to the other end (connected to conductor 53) (which in turn is connected to the Vcc power supply) and one lead being attached to wiper arm 54. In operation, a user depresses a selected point along strip 50 in order to "pick off" a predetermined resistance from resistive element 52. Thus, the voltage appearing on conductor 54 is changed by depressing selected points along the strip.

Considering further structure illustrated in FIG. 2, the leads from selection strip 50 are provided via connector 56 to a programmable microprocessor 58. The microprocessor includes an analog-to-digital converter for changing the analog voltages on conductor 54 to digital values. Processor 58 is received within housing 12, such being illustrated by dashed lines in FIG. 2. All of the components within the dashed lines in FIG. 2 are either mounted on or received within housing 12. Voltage provided by a power supply (not shown) is illustrated by the notation Vcc and ground is schematically illustrated by the usual symbol. The microprocessor output is applied to a conductor 60 which in turn is provided to one input of a conventional gate 62.

The output of gate 62 is provided to a commercially available interface chip 64. Chip 64 includes thereon two TTL to RS 232 converters and two RS 232 to TTL converters. The output of gate 62 is connected to an input of a TTL to RS 232 converter and the output of that converter appears on a conductor 66. Data from keyboard/display 14 appears on an output connected to a conductor 68 which, in turn, is connected to one input of an RS 232 to TTL converter on chip 64. The output of that converter appears on a conductor 70 and is applied to the other input of gate 62. Since microprocessor 58 generates serial TTL signals while keyboard/display 14 generates RS 232 signals, chip 64 is used to convert the keyboard/display RS 232 signals to TTL, such converted signals appearing on line 70. Gate 62 combines the signals from processor 58 and display/keyboard 14 and provides the same to interface 64 which, in turn, produces a combined RS 232 signal on conductor 66, the same being supplied to a commercially-available computer 72 via connector 74. RS 232 data from computer 72 may, in turn, be supplied via conductor 76 to keyboard/display 14.

Prior to considering the manner in which the instant embodiment of the invention is operated, attention will first be given to the nature of the job in connection with which the instant embodiment of the invention is used. One aspect of developing geological information includes drilling a wellbore with a drilling system which preserves core taken from the bore. Some such systems generate thousands of feet of core. In addition to various mechanical and chemical testing of the core, it is desirable to collect data concerning the appearance of the core. Such data is typically correlated to a well depth, measured in feet, and includes a description of observable characteristics in categories such as grain size, grain relief, color, pore fluid components, etc. A number of descriptors within each category may be used to describe a core sample from a particular depth. The color, for example, may be black, blue, brown, gray, etc.; the grain size may be clay-sized, silt-sized, gravel-sized, etc., and the grain relief may be smooth, striated, faceted, etc.

In FIG. 1, a page like illustrated page 48 can be representative of a category (i.e., sedimentary rocks) like the foregoing, with the various descriptors thereunder, e.g., silt stone, shale, marl, etc., comprising descriptors for that particular category. Each additional page contained in the book includes a separate category with a plurality of descriptors for each. A geologist can, by observing and recording such information, develop data of significance in interpreting the nature of the formation from the which the core was extracted.

Figure 3:
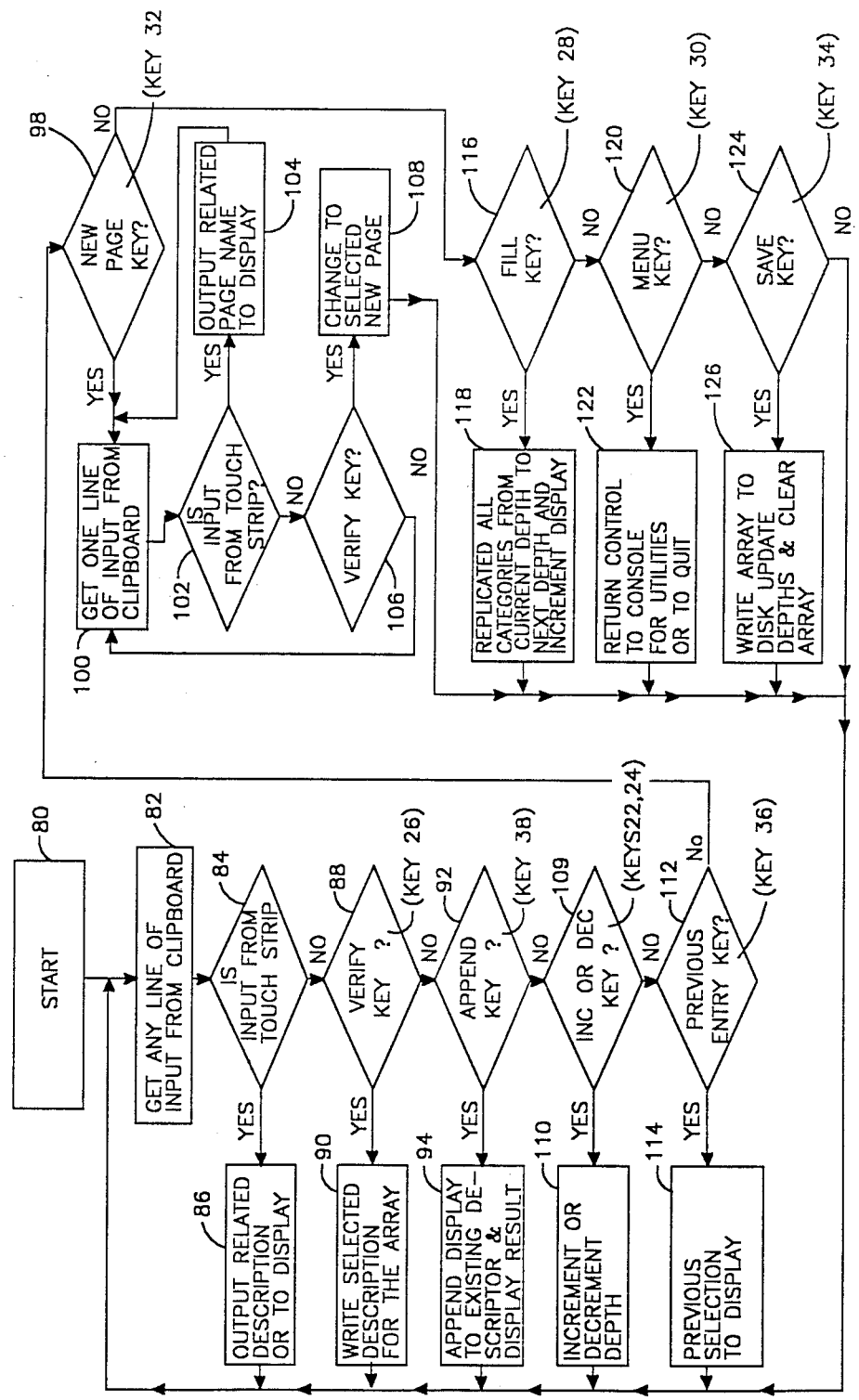
FIG. 3 is a computer program flow chart illustrating a computer program contained in the memory of the schematically-illustrated computer of FIG. 2.

Turning attention now to FIG. 3, consideration will be given to the operation of the instant embodiment of the invention in connection with a description of a computer program, a flow chart of which is indicated generally at 78 in FIG. 3, stored in a memory of computer 72 in FIG. 2. Block 80 in the flow chart indicates that the program is started by entering a "start depth" and "end depth" at the console of computer 72. The start depth is the well depth, in feet, from which the next core sample to be observed was extracted. The end depth can be any depth up to 20 feet greater than the start depth. So starting the program creates an array in a memory in computer 72 having up to 20 rows (one for each foot between the start depth and end depth) in which descriptors relating to the characteristics of a core sample taken from the associated depth are stored.

The program automatically initiates in the "color" category. In other words, the first descriptor(s) to be entered into the memory array in computer 72 are those contained on the "color" page on device 10 (the clipboard). Thus, when first started, display 16 shows only the current depth, in the present example, 3110 ft, from which the core sample under observation was taken and the word "color." Signals causing the word "color" to appear on the display are provided from computer 72 to keyboard/display 14 via conductor 76. Next, the operator can flip through the pages, like pages 46 and 48, comprising the book on the clipboard until the color page, page 48, is positioned adjacent strip 50 as shown in FIG. 1. The operator then observes the core and depresses strip 50 adjacent the descriptor, in this case a particular color, which most accurately describes the core color. Thus, when the touch strip adjacent the work "red" is depressed, a predetermined voltage level is applied to an input of processor 58 via conductor 53. The analog-to-digital converter contained within processor 58 converts the same to a digital value and serially applies that value to conductor 60. Gate 62 combines the TTL signals on conductor 60 with the signal, if any, on conductor 70 and applies the combined signal to an input on chip 64 for converting the combined TTL signal to RS 232 which is then placed on conductor 66 and provided to computer 72. Processor 58 provides a "#" identifier at the beginning of each digital value it generates, thus designating the same as a signal from the touch strip. When computer 72 identifies a digital signal as being generated by the touch strip, it looks in a touch strip look-up table, referred to herein as a data matrix, in a memory of computer 72, extracts a descriptor associated in the table with the particular digital value, in this case "red" in the "color" category, and provides a digital signal on conductor 76 to keyboard/display 14 which causes the descriptor to appear on display 16. Thus, "red" appears adjacent "3110" on display 16.

The foregoing is accomplished in the flow chart beginning in block 82, at which point computer 72 receives data on conductor 66. Thereafter, in diamond 84, computer 72 checks for the "#" to see if the data is from the touch strip. If so, in block 86, the computer generates a signal (from the look-up table), indicative of the selected descriptor, which is applied to conductor 76 causing the appropriate descriptor name to appear on display 16.

If the display shows the descriptor which the operator wishes to be preserved in connection with the core under observation, VERIFY key 26 is pressed. In the flow chart, diamond 88 refers to the VERIFY key. When the same is pressed (in block 90), a signal is applied to computer 72 via conductors 68, 70, and 66 causing the program to write the displayed descriptor to the memory array defined initially in block 80.

It should be noted that after a descriptor is placed on the display, in block 86, the program again returns to block 82 for a new line of input, i.e., data is taken from conductor 66. The same is true after data is written to the array in block 90.

If after depressing VERIFY key 26 in diamond 88 when the "red" descriptor is displayed, the operator chooses to utilize more than one descriptor in the category under consideration, touch strip 50 is depressed adjacent the additional descriptor. Thereafter, APPEND key 38, in diamond 92, is depressed thereby applying a signal to computer 72 via conductors 68, 70, and 66. In block 94, the program then displays, via signals on conductor 76, the previously entered descriptor combined with the currently selected descriptor on display 16. By way of example, in FIG. 1, the word "banded," also from page 48, is appended to "red." Thereafter, the program returns to block 82 to get an additional line of input on conductor 66. If the displayed combination is that which the operator desires to store, VERIFY key 26 (indicated in diamond 88) is depressed thereby storing the displayed combination in the array in computer 72.

One of the commands, illustrated in diamond 98, and referring to NEW PAGE key 32 in FIG. 1, is to indicate when a new page is placed in the page bay. A new page is selected by punching key 32, thereby placing the program in diamond 98, and thereafter touching strip 50 adjacent a mark, like mark 96, on page 48. Each page has a different single mark, like mark 96, along the edge thereof at a different position along strip 50. Thus, after NEW PAGE key 30 is depressed, touch strip 50 is depressed adjacent the mark on the page of interest. A NEW PAGE look-up table in a memory in computer 72 associates each voltage level generated by the touch strip, after NEW PAGE key 32 is depressed, with the name of the category, e.g., "color," on the selected page. The program gets a line of input from conductor 66 (in block 100) and if the same is from the touch strip (as determined in diamond 102), the name of the category on the selected page is located in a look-up table, also referred to herein as a data matrix, and is displayed, via conductor 76, on display 16 (indicated in block 104). If the category shown on the display is that in which the operator would like to enter one or more descriptors relating to the core under observation, the VERIFY key is depressed (in diamond 106) and the program causes future descriptor searching (in response to touch strip signals) to be done in a look-up table, also referred to herein as a data matrix, associated with the newly selected page or category, such being illustrated in block 108. Thereafter, the program returns to block 82 for entry of one or more descriptors associated with the category or page in the page bay.

After the operator has entered descriptors from all of the categories or pages, or from as many categories or pages as is appropriate for the core sample under consideration, increment key 24 is depressed, illustrated in diamond 109, to add one foot to the displayed depth. When key 24 is depressed, signals via conductors 68, 70, and 76 to computer 72 cause the program to generate signals that are applied to conductor 76 which add one foot to the displayed depth on keyboard/display 14. Observation then shifts to the next core sample, that being core from one foot deeper in the well, and the process as previously described is implemented for the core sample under observation. It should be noted that the 20 ft array originally created in block 80 can be written over at any time by the operator. In other words, if the operator decides that some previously described core should be described in a different fashion or that descriptors from other categories (pages) which were not entered should be entered, the operator may depress the increment or decrement key 22 to move forward or back in one foot increments from the displayed level. The depth can be decremented to the start depth as selected in block 80 or to any depth between the start depth and the end depth and thereafter descriptors in categories which were not previously entered may be entered (or previously entered descriptors may be written over with different descriptors). Commands by keys 22 and 24 are illustrated in block 110. After so changing the depth, a line of input is again taken from conductor 66 in block 82.

Core samples from many feet are sometimes substantially the same because of the similarity of the adjacent formations from which the core is taken. If such is the case, PREVIOUS ENTRY key 34 (in diamond 112) may be depressed thereby causing the program to display (in block 114) the descriptor(s) entered in connection with the selected page for the previously-displayed depth. If the operator wishes to store the previous descriptor(s) in connection with the description of the current core, VERIFY key 26 (in block 88) is depressed thereby writing the same to the array. Thus, in the example under consideration, the information "red:-banded" appears at 3110. If the PREVIOUS ENTRY procedure in diamond 112 is followed at 3111 ft when the "color" page is selected and is verified, the same entry appears in the array for the color category for 3111 ft.

In some instances, adjacent core samples may be substantially the same in all observable respects. If such is the case, FILL key 28, represented in diamond 116, is depressed thereby causing the program to duplicate in the array in computer 72 all of the descriptors (in each category) associated with the current depth for the next foot, such being indicated in block 118.

If when input is taken from the clipboard in block 82 (via conductor 66), it is determined that MENU key 30, illustrated in diamond 120, is depressed, control is transferred to the console of computer 72 to permit such functions as resetting the start and end depth, quitting the program, reviewing the stored data, etc., such being illustrated in block 122. Control can be returned to the clipboard by pressing one of the console keys thereby initiating functions illustrated in diamonds 84, 88, 92, etc.

Computer 72 includes a commercially-available hard disk memory (not shown) into which the current 20 ft array may be written by depressing SAVE key 34, such being illustrated in diamond 124. When such occurs, the contents of the 20 ft array is transferred to the disk, the start depth selected in block 80 is updated to the selected end depth plus one foot, the end depth is updated to the new start depth plus 20 ft and the array is cleared, thus preparing the clipboard for data entry for the next 20 ft of core samples. The foregoing is illustrated in block 126. Thereafter, control is transferred to block 82, a new line of input is taken from the clipboard and operation proceeds as previously described in connection with the entry of descriptors relating to the next core sample.

Referring now to FIG. 4, illustrated therein is a sample of print-out of data stored on a hard disk, as previously described, in connection with observation of actual core samples taken from between 550 and 577 ft in a well bore. The categories are separated by OR bars while descriptors appended together are separated by colons. When no data appears between a pair of adjacent OR bars, descriptors were not entered in that particular category. It can be seen that a total of 19 categories, each category being represented by a page in the book on the clipboard in FIG. 1, are available. The first category relates to the formation type with the next category in FIG. 4 in which a descriptor is entered relating to color. It can be seen that the append function was used in connection with each descriptor used in the color category, such being used to indicate the shade of the selected color.

Although not illustrated in the flow chart of FIG. 3, a line of comments typed on the keyboard of computer 72 may be inserted between adjacent depths. Thus, if some unusual condition or observation is noted by the operator, a comment concerning the same may be stored in the array adjacent the depth of interest.

Figure 5:
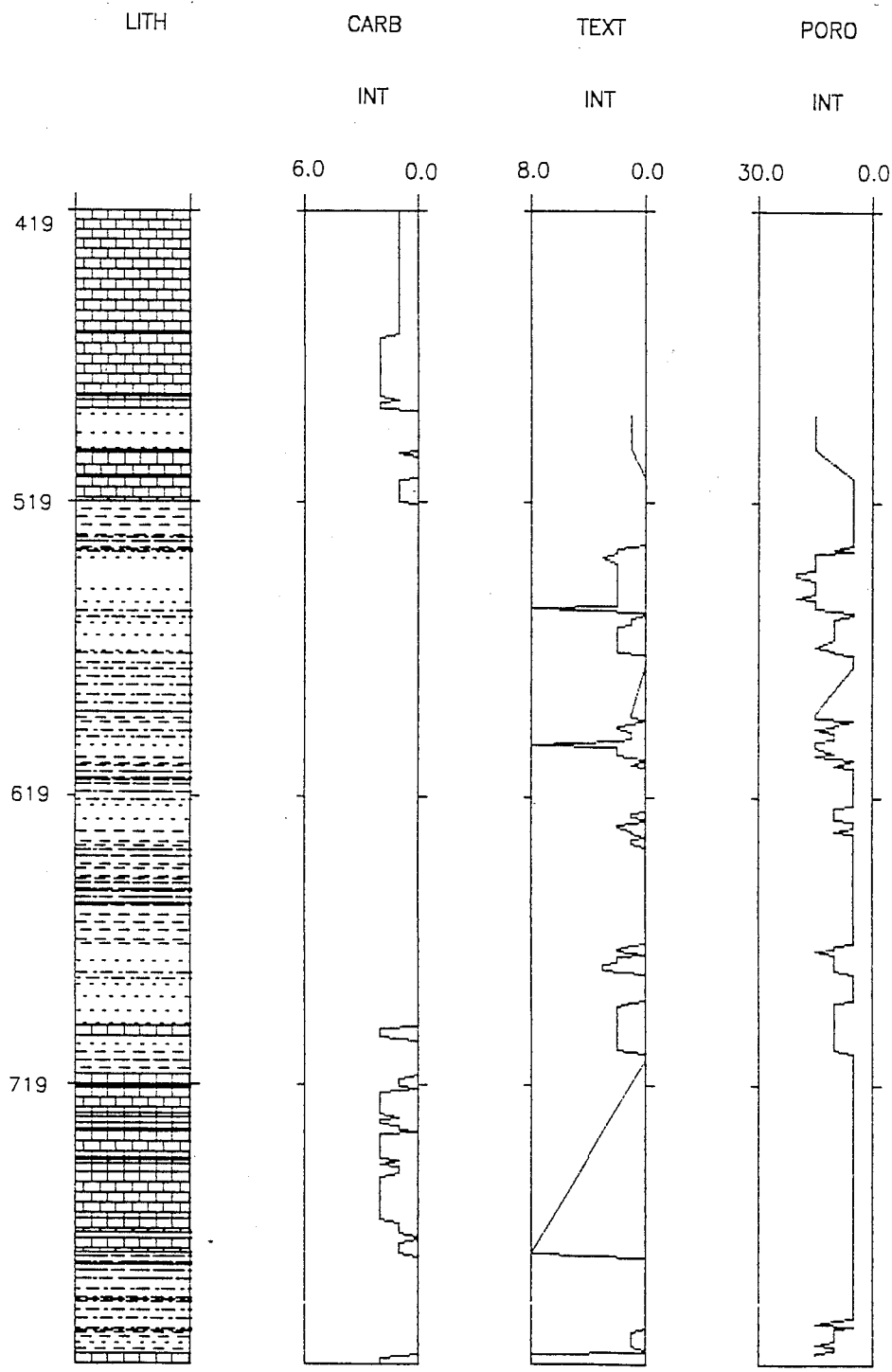
FIG. 5 is an example of one manner of displaying data similar to that shown in FIG. 4.

Turning now to FIG. 5, illustrated therein is a graphic display of data collected in accordance with the instant embodiment of the invention. The data is manipulated by a computer program, different from that illustrated in FIG. 3, which a person having ordinary skill in preparation of graphics computer programs could easily prepare an order to illustrate, by depth, the data collected with the instant embodiment of the invention.

Thus, a data entry method and apparatus has been described which is small, lightweight, and especially adapted for field use. The instant embodiment of the invention may be held on the lap of a user as descriptors relating to the observed characteristics of core samples are entered as described. In addition, the simplicity of use makes this system ideal for use by operators who are either unable or unwilling to enter computer commands and data using a conventional alpha-numeric keyboard and monitor in connection with a computer which has been programmed to receive and manipulate data.

The ease of use is, in part, facilitated by the hardcopy menu having a linear array of descriptors thereon adjacent a linear selection means, the touch strip in the instant embodiment of the invention. Such enables an operator to depress the touch strip with his or her forefinger and rapidly move the same up and down the strip thereby rapidly changing the selected descriptor on the display. With a small amount of practice, an operator can become adept at rapidly "picking off" a descriptor of interest on the touch strip. Another advantage of a hardcopy sheet from which descriptors may be selected is that in addition to words, graphic symbols, colors, textures, and the like may be used on the hardcopy and selection of such may be made, as in the instant embodiment of the invention, by depressing a touch strip adjacent the descriptor of interest. Nonword descriptors, such as textures, cannot be displayed on a computer monitor. Although color monitors do exist, much more information concerning color shades can be shown on a hardcopy menu, as described herein, than on a monitor.

Thus, the invention permits rapid data entry by relatively unskilled personnel under field conditions and at the same time has very few components and may be easily and inexpensively manufactured.

It is to be appreciated that additions and modifications may be made to the foregoing detailed description of the preferred embodiment of the method and apparatus of the invention without departing from the spirit of the invention, which is defined in the following claims.

I claim:

1. An apparatus for simplifying the recording and storage of visual characteristics of core removed from a borehole, said apparatus comprising:
   a book having a plurality of pages on which are recorded a number of preselected categories and characteristics which are determined by observation of core removed from a borehole, said book being mounted on a person-holdable housing;
   selection means mounted on said housing adjacent said book, for selecting a page and for selecting a characteristic on a page to which said book is opened;

display means mounted on the housing for displaying a selected depth value and for displaying characteristics of core selected for the selected depth value;

means for increasing the selected depth value by increments;

a first command key mounted on the housing for operating the means for increasing the selected depth value by increments to increase the selected depth value by increments;

means for decreasing the selected depth value by increments;

a second command key mounted on the housing for operating the means for decreasing the selected depth value by increments to decrease the selected depth value by increments;

means for repeating selected characteristics selected for core at the selected depth value for an incremented depth value;

a third command key for operating the means for repeating selected characteristics to repeat said selected characteristics for an incremented depth value;

means for repeating all of the characteristics selected for core at the selected depth value for an incremented depth value;

a fourth command key for operating the means for repeating all of the characteristics selected for core at the selected depth value for an incremented depth value to repeat all of said characteristics at the incremented depth value; and memory means for creating an array of selected characteristics of a core sample as a function of depth values from operation of means aforesaid.

2. The apparatus of claim 1, wherein said selection means includes a linear array of actuating positions, a different one of such positions being associated with each characteristic on a page to which said book is opened.

3. The apparatus of claim 1, wherein said apparatus further includes a look-up table comprising data corresponding to the characteristics printed on said book pages, said table being stored in said memory means.

4. The apparatus of claim 1, wherein said selector means comprises a linear potentiometer.

5. A data input device according to claim 1, wherein said device further comprises a verifier for verifying one or both of the selected page and the selected data input.

6. A data input device according to claim 5, wherein said verifier comprises one of a visual display, auditory signal, voice back system.

7. A data input device according to claim 1, which further comprises appender means for appending together as a single data input two or more characteristics from a selected page.

8. The apparatus of claim 1 wherein the recorded preselected characteristics comprise descriptors capable of display on or attachments to a page selected from one or more of graphic symbols, natural language descriptors, physical analog descriptors, colors, textures, surfaces, and tactile symbolic descriptors.

* * * * *

UNITED STATES PATENT AND TRADEMARK OFFICE
CERTIFICATE OF CORRECTION

PATENT NO. : 4,973,960

DATED : November 27, 1990

INVENTOR(S) : Houston B. Mount, II

It is certified that error appears in the above--identified patent and that said Letters Patent is hereby corrected as shown below:

In the Abstract, line 2, after "notebook" insert --having--.

Signed and Sealed this

First Day of December, 1992

Attest:

DOUGLAS B. COMER

*Attesting Officer*     Acting Commissioner of Patents and Trademarks